United States Patent
Abrahamson

(10) Patent No.: US 6,428,513 B1
(45) Date of Patent: *Aug. 6, 2002

(54) CATHETER HUB ANCHORING DEVICE

(76) Inventor: Timothy Alan Abrahamson, 8027 S. 134th St., Seattle, WA (US) 98178

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 547 days.

(21) Appl. No.: 08/761,422

(22) Filed: Dec. 6, 1996

Related U.S. Application Data

(60) Provisional application No. 60/009,490, filed on Dec. 15, 1995.

(51) Int. Cl.[7] .............................................. A61M 5/32
(52) U.S. Cl. ..................................................... 604/174
(58) Field of Search ................................ 604/174, 178, 604/180, 179; 128/DIG. 26, 26

(56) References Cited

U.S. PATENT DOCUMENTS

| | | | | |
|---|---|---|---|---|
| 2,173,527 A | | 9/1939 | Agayoff ...................... 128/349 |
| 2,409,432 A | | 10/1946 | Hubbard .................... 128/216 |
| 3,176,690 A | * | 4/1965 | H'Doubler .................. 604/174 |
| 3,210,816 A | * | 10/1965 | Clemons ................. 604/174 X |
| 3,374,509 A | * | 3/1968 | Logan et al. ........... 604/174 X |
| 3,459,175 A | * | 8/1969 | Miller ..................... 604/174 X |
| 3,461,869 A | * | 8/1969 | Hargest ............... 128/DIG. 26 |
| 3,575,160 A | * | 4/1971 | Vass ....................... 604/174 X |
| 3,921,631 A | | 11/1975 | Thompson ............... 128/214.4 |
| 3,957,082 A | * | 5/1976 | Fuson et al. ............ 604/174 X |
| 3,976,080 A | * | 8/1976 | Bornhorst et al. ................ 128/DIG. 26 X |
| 4,129,128 A | | 12/1978 | McFarlane .................. 128/133 |
| 4,134,402 A | | 1/1979 | Mahurkar ............... 128/214 R |
| 4,149,539 A | | 4/1979 | Cianci ........................ 128/325 |
| 4,366,817 A | | 1/1983 | Thomas ..................... 604/174 |
| 4,435,174 A | * | 3/1984 | Redmond et al. ........... 604/174 |
| 4,534,760 A | | 8/1985 | Raible ........................ 604/175 |
| 4,543,087 A | | 9/1985 | Sommercorn et al. ........ 604/43 |
| 4,643,711 A | | 2/1987 | Bates ............................. 604/4 |
| 4,650,473 A | * | 3/1987 | Bartholomew et al. ..... 604/174 |
| 4,682,978 A | | 7/1987 | Martin ......................... 604/43 |
| 4,772,268 A | | 9/1988 | Bates .......................... 604/174 |
| 4,894,057 A | | 1/1990 | Howes ........................ 604/280 |
| 5,106,368 A | | 4/1992 | Uldall et al. .................. 604/43 |
| 5,107,856 A | * | 4/1992 | Kristiansen et al. ................ 128/DIG. 26 X |
| 5,237,988 A | * | 8/1993 | McNeese ......... 128/DIG. 26 X |
| 5,348,536 A | | 9/1994 | Young et al. ................. 604/43 |

* cited by examiner

Primary Examiner—Michael J. Hayes
Assistant Examiner—Kevin C. Sirmons
(74) Attorney, Agent, or Firm—Pierce Atwood

(57) ABSTRACT

An elongate catheter having one or more lumens therein and at least one lumen in flow communication with a hub member including one or more loop members extending laterally from a tubular member thereof such that a securement area is formed by the opening between the body of the tubular member and the loop member which is significantly larger than currently available catheters. The loop members are formed to provide a soft and flexible area for securing the catheter to the body of the patient wherein the securement area is spaced apart from the body of the hub member and the loop members may be easily removed to allow the catheter to be removed from the body of the patient.

20 Claims, 6 Drawing Sheets

CATHETER HUB ANCHORING DEVICE

This application claims the benefit of U.S. provisional application No, 60/009,490, filed Dec. 15, 1995.

FIELD OF THE INVENTION

The present invention relates to catheters and more particularly to a catheter having one or more lumens therein and an integral anchoring mechanism along the hub member of the catheter to facilitate suturing and removal of the catheter from the body of the patient.

BACKGROUND OF THE INVENTION

Single or multiple lumen catheters are well known in the medical field and are widely used in medical procedures such as hemodialysis or other procedures wherein it is desirable to inject or remove fluids through one or more lumens of the catheter. For example, in hemodialysis it is desirable to remove blood from a vein or other vessel of a patient through a first lumen of a catheter while returning a corresponding amount of dialyzed blood to the patient through another lumen of the catheter. In certain situations, it may also be desirable to have a third lumen extending through the catheter to allow a medication to be injected therethrough without interfering with the operation of the first or second lumens.

The currently available single or multiple lumen catheters typically include a distal section having a tip member thereon; an elongate body portion which extends proximally from the tip portion; a catheter hub or hub member on the proximal end of the body portion; and one or more extension members which are used to inject and/or remove fluids from the catheter. Additionally, if the catheter is intended to be used for longer term therapy, such as in long term dialysis applications in excess of thirty days, the body portion of the catheter may also include a cuff thereon to allow the tissue of the patient to grow into the cuff. The growth of the tissue into the cuff of the longer term catheter helps to seal the catheter tunnel tract and also stabilizes the catheter in the body of the patient. The hub member of the catheter is frequently sutured to the body of a patient to minimize the movement or migration of the catheter in the catheter tunnel tract of the patient and secondarily to inhibit movement of the distal end of the catheter in the blood vessel of the patient once the catheter has been inserted to the desired position.

Various catheter hub designs have been used to facilitate the attachment of the catheter to the body of the patient. These designs may be grouped generally into designs which allow the physician to wrap the suture through the skin of the patient and around the catheter hub; designs which provide tab members which enable the physician to pass the suture through the skin of the patient and the tab member or designs which allow both.

In catheters which are intended to be used in a patient for relatively long periods of time, the hub member functions as a temporary method of limiting the movement of the catheter while tissue is allowed to grow into a cuff member which is located on the catheter body. With the longer term catheters, a physician may remove the suture from around the hub member approximately one week after the catheter was implanted into the patient so that the catheter is retained in the desired position by the tissue of the patient which has grown into the cuff in the catheter tunnel tract. In short and long term catheters, it is occasionally necessary for the physician to reposition the catheter or remove the catheter from the body of the patient; therefore, it is desirable to provide an attachment mechanism which provides secure and flexible attachment of the catheter to the body of the patient while allowing for the easy removal of the catheter from the body of the patient when necessary. Although the prior hub member designs which allow the physician to wrap the suture around the hub member of the catheter are simple to use, these designs have the disadvantage that the suture has a tendency to pull out of the skin of the patient if the patient moves excessively or accidentally bumps the proximal portion of the catheter. With these designs, the suture may also damage the hub member if the suture is wrapped or tied too tightly around the hub member. Additionally, it is more likely that the physician may accidentally cut or nick the hub member of this design while attempting to secure the catheter to the skin of the patient or during removal or repositioning of the catheter member than with other hub member designs. Another disadvantage to this type of hub member design is that inconsistent hub rotation forces may arise depending on the how tightly the suture is tied around the hub member.

In the catheter hub member designs which allow the physician to wrap the suture through tab members, the suture is threaded through the skin of the patient and then through the openings in the tab members. The ends of the suture are then tied together to secure the tab member and catheter to the patient. In this type of design, it is important that the tab members have sufficient flexibility to allow the tab members to flex in response to movement of the patient in order to avoid tearing the suture from the skin of the patient or irritating the patient at the suture location. Another consideration in this type of hub member design is that the tab members must have sufficient strength to prevent the suture from cutting the tab members and pulling out of the tab members. Additionally, it is important to have openings in the tab members which are sufficiently large to allow the physician to easily pass the suture through the opening in the tab member at the end of the placement procedure. Finally, it is important for the hub member design to allow for the easy and rapid removal of the sutures from the tab and hub members and the body of the patient. Various commercially available catheter hub member designs of the type described above are shown in FIGS. 1–6, none of which meet all of the preferred characteristics for a hub member.

The hub member of the present invention meets the preferred characteristics and overcomes the disadvantages described above by providing loop members which have an increased relative flexibility while providing an enlarged opening to allow for suturing between the hub member and the loop member. The loop member of the present invention still maintains the structural strength necessary to prevent to suture from tearing through the loop members if the patient moves excessively and provides sufficient flexibility to accommodate normal movement of a patient without tearing the skin of the patient.

The loop members of the present invention are also designed to be easily cut off flush with the side of the catheter once the tissue of the patient has grown into the cuff on the body portion of the long term catheter while minimizing the likelihood that the catheter body or hub member will be nicked or cut during removal of the loop members.

In one form of the present invention, the loop members are also designed to be rotatable with respect to the body of the catheter in short term catheters to allow the catheter to be easily rotated or repositioned with respect to the skin of the patient while minimizing the likelihood that the catheter body or hub member will be nicked or cut during rotation or repositioning of the loop members.

SUMMARY OF THE PRESENT INVENTION

The present invention is directed to an improved design for securing the hub member of the catheter to the body of a patient. This design, when used properly, reduces migration and movement of the catheter relative to the catheter tunnel tract of the catheter in the skin of the patient and minimizes the likelihood that the suture will be torn from the skin of the patient during normal patient movement. Additionally, the securement points or loop members are spaced apart from the catheter body and hub member to reduce the likelihood that the catheter body and/or hub member will be damaged during the placement, repositioning and removal procedures.

In one form of the present invention, the hub member is preferably formed of a flexible or elastomeric material such as a silicone or similar material and includes a tubular shaped member having a pair of generally loop shaped members which may be formed of a material which is similar to the material of the tubular member. The loop members preferably extend laterally from the sides of the tubular member and are preferably formed or otherwise bonded or affixed as part of the tubular member. The tubular member and loop members may also be formed as a separate or integral part of the hub member of the catheter. The cross sectional and inner and outer diameter dimensions of the tubular member and loop members may be readily modified to form loop members having the desired design features such as moderate stiffness, increased cut resistance and increased patient comfort.

In an alternate form of the hub member of the present invention, the tubular member and loop members are preferably rotatable with respect to the body of the catheter. In this embodiment, the tubular member may be rotatable with respect to the hub member and body portion of the catheter while the longitudinal and/or lateral positioning of the tubular member with respect to the catheter body is maintained by receiving a portion of the tubular member in a groove and recess or similar feature on the hub member and tubular member.

The hub member of the present invention is preferably used with a single or multiple lumen catheter such as a dual or triple lumen catheter which may be used for infusion, apheresis and/or hemodialysis treatments of the patient. The catheter may also preferably include at least one generally D-shaped lumen therein. If the hub member is used with an infusion, apheresis and/or hemodialysis catheter the body portion of the catheter preferably includes a blood return or first lumen which extends between the proximal end of the body portion of the catheter and a distal opening on the catheter tip which is located at the distal end of the catheter. The intake or secondary lumen of this type of catheter preferably extends between the proximal end of the body portion of the catheter and a side opening which is preferably located along the distal portion of the catheter and is generally proximal to the catheter tip.

An object of the present invention is to provide a hub member which includes a tubular member having a pair of loop members thereon to provide improved flexibility between the secured catheter and the skin of the patient while limiting movement of the catheter relative to the catheter tunnel tract and/or exit site.

Another object of the present invention is to provide a hub member having a pair of loop members thereon which are shaped and oriented with respect to the hub member to allow for the easy removal of the loop members from the hub member to enable the easy detachment of the hub member from the skin of the patient.

Yet another object of the present invention is to provide enlarged openings between the tubular member and the loop members of the hub member to allow for the easy passage of the suture therethrough as the hub member is attached to the body of the patient.

Yet another object of the present invention is to provide a hub member having flexible loop members extending laterally therefrom to minimize the likelihood of the suture being torn from the skin of the patient during normal movement of the patient.

Yet another object of the present invention is to provide enlarged openings between the tubular member and the loop members of the hub member to minimize the bulk and weight of the hub member.

DESCRIPTION OF THE PREFERRED EMBODIMENTS

Figure 1:
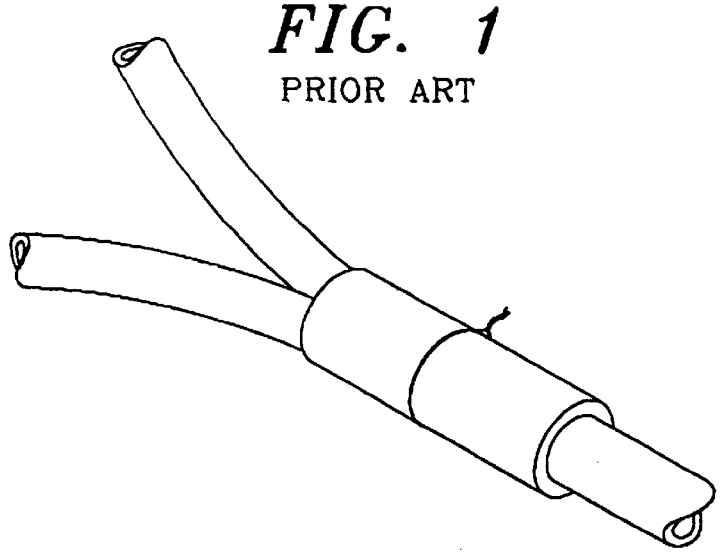
FIG. 1 is an elevated partial side view of a prior art catheter wherein the hub member is sutured to the skin of the patient.
Figure 2:
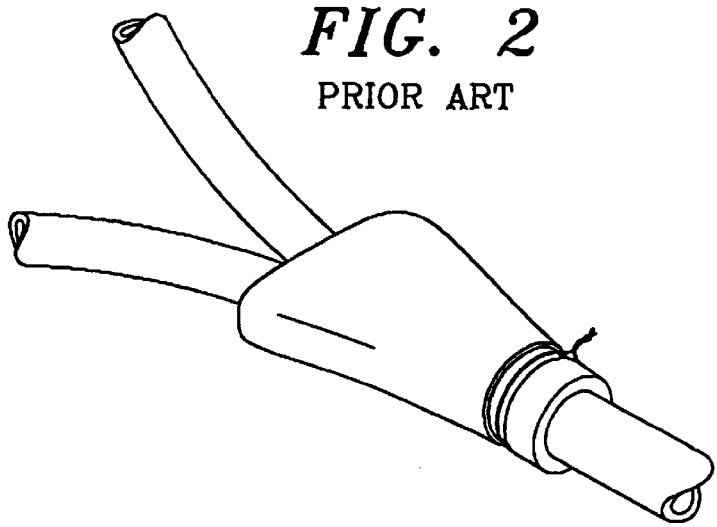
FIG. 2 is an elevated partial side view of a prior art catheter wherein the hub member includes a circumferential groove member thereon and is adapted to be sutured directly to the skin of the patient.
Figure 3:
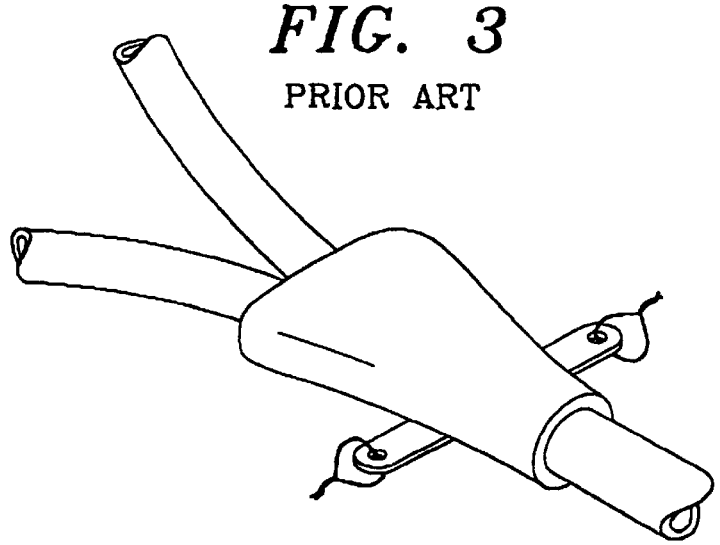
FIG. 3 is an elevated partial side view of a prior art catheter wherein the hub member includes an integral suture wing formed thereon and the suture wing is adapted to be sutured to the skin of the patient.
Figure 4:
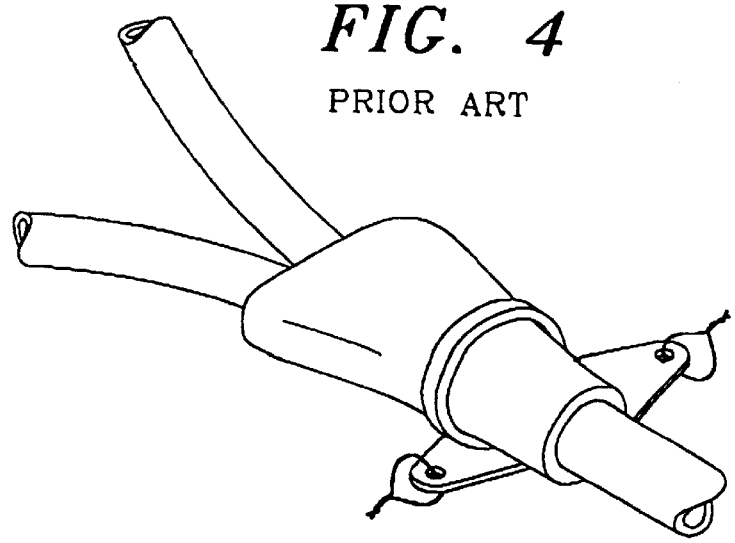
FIG. 4 is an elevated partial side view of a prior art catheter wherein the hub member is rotatable about the body portion of the catheter and includes a separate suture wing thereon and the suture wing is adapted to be sutured to the skin of the patient.
Figure 5:
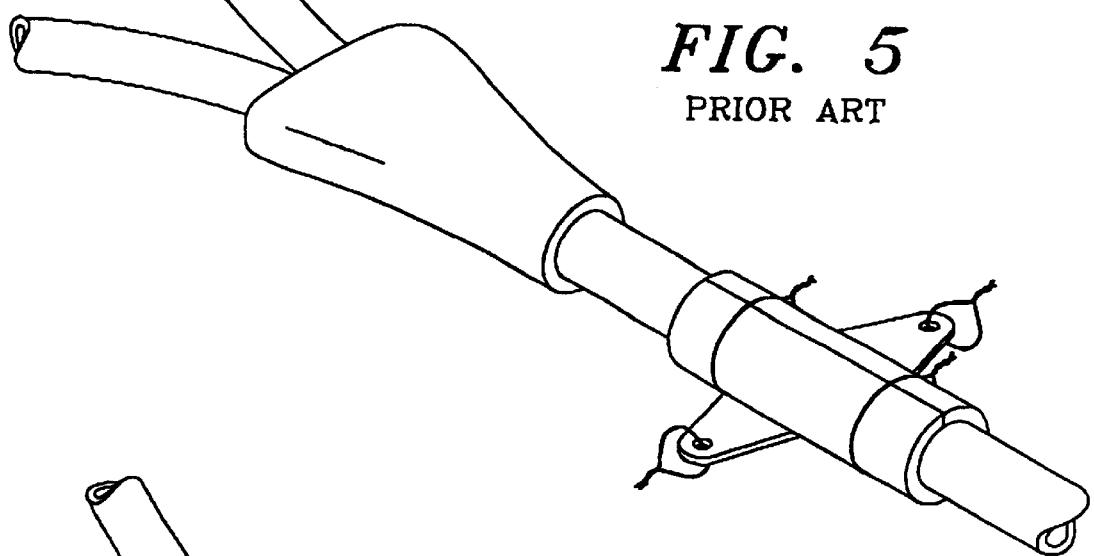
FIG. 5 is an elevated partial side view of a prior art catheter wherein the hub member includes a tubular member having an integral suture wing thereon attachable to the hub member and the suture wing is adapted to be sutured to the skin of the patient and the tubular member is adapted to be sutured in the closed position around the hub member.
Figure 6:
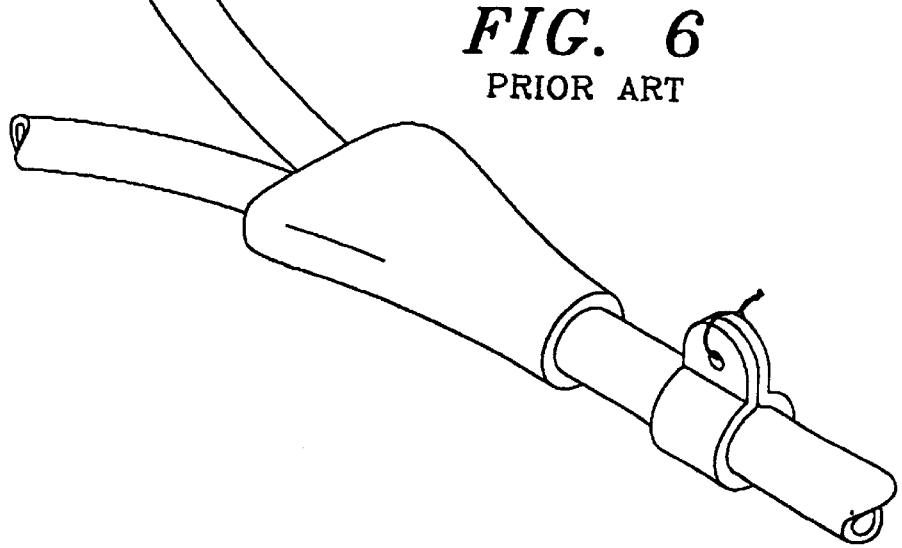
FIG. 6 is an elevated partial side view of a prior art catheter wherein the hub member includes a tubular member having an integral suture wing thereon and the tubular member is adapted to be folded about the body portion of the catheter and the folded suture wing is adapted to be sutured to the skin of the patient.
Figure 7:
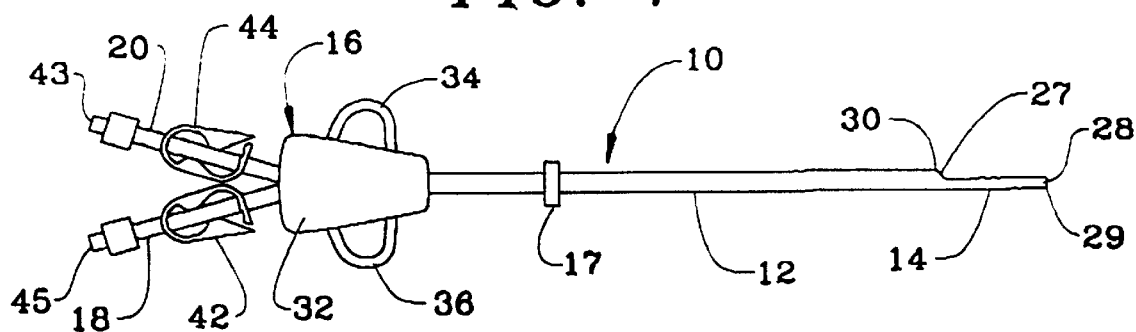
FIG. 7 is an elevated side view of a round catheter having an embodiment of the catheter hub member of the present invention thereon.
Figure 8:
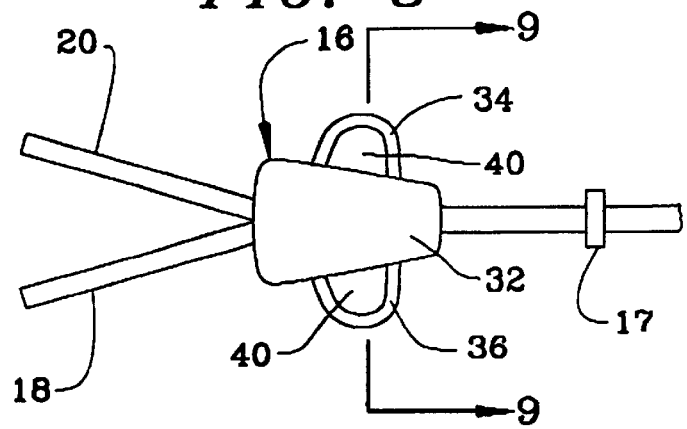
FIG. 8 is an enlarged side view of the catheter of the embodiment shown in FIG. 7 showing the preferred embodiment of the catheter hub member of the present invention.

As shown in the drawings, a generally preferred form of the overall catheter assembly 10 of the present invention is generally similar to the multiple lumen catheters shown in U.S. Pat. No. 5,403,291 granted to Abrahamson on Apr. 4, 1995 and which is commonly owned with the present invention. The catheter assembly 10 shown in FIGS. 7–10 generally includes an elongate body portion 12 having a round cross-section with a tip member 14 on the distal end thereof and a Y-shaped connector or hub member 16 on the proximal end thereof. As shown in FIG. 7, the catheter assembly 10 of the present embodiment preferably includes a cuff member 17 on the body portion 12 and is particularly useful for long term use; i.e., implantation in excess of thirty days. As shown in FIG. 7, the proximal end of the hub member 16 includes extension members 18 and 20 thereon. As used herein, the term "proximal" is intended to refer to the end or portion of a member which is normally oriented or positioned away from the patient while the term "distal" refers to the end or portion of a member in use which is nearest to the patient. Although a preferred form of the present invention is described herein with respect to multiple lumen catheters, it is intended that the present invention may also be used with nearly any catheter having one or more lumens therein including catheters used for infusion, apheresis, angiographic or diagnostic procedures.

Figure 13:
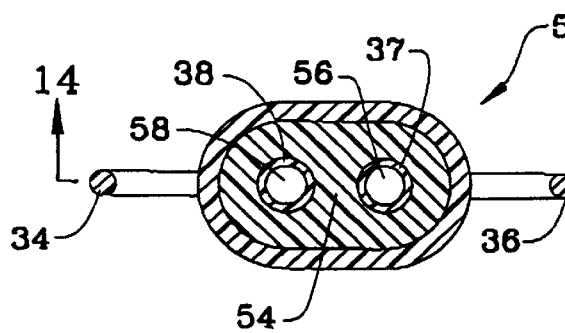
FIG. 13 is a cross-sectional view of the catheter hub member shown in FIG. 11 taken generally along lines 13—13 of FIG. 12.
Figure 14:
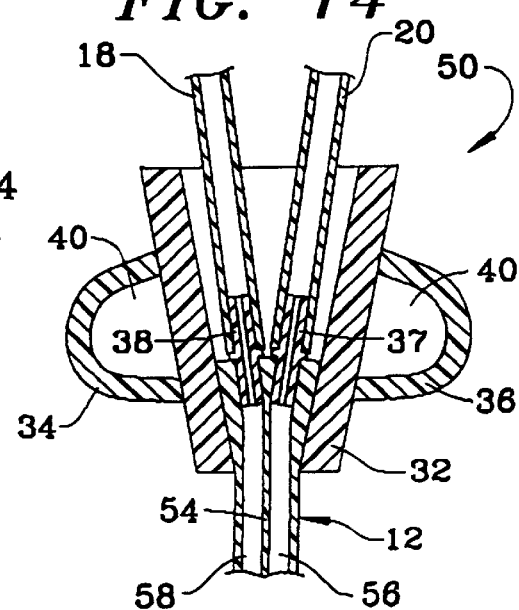
FIG. 14 is a longitudinal cross-sectional view of the catheter hub member shown in FIG. 11 taken generally along lines 14—14 of FIG. 13.

The body portion 12 may be of nearly any cross-sectional form including the round shape of the preferred embodiment (FIG. 9) or the generally oval cross-sectional shape shown in FIG. 13. The body portion 12 of the catheter assembly 10 is preferably hollow except for a septum 22 which divides the interior of the elongate member into two or more lumens which are preferably lumens that are identified as 24 and 26 and are generally parallel to each other. The lumens of the preferred embodiment may be formed by a generally flat, longitudinal septum, with each lumen, 24 and 26, having a generally D-shaped cross section. As illustrated by the arrows in FIG. 8, the lumen 24 is preferably the blood intake or arterial lumen, and the lumen 26 is preferably the blood return or venous lumen when the catheter assembly is used for dialysis or similar procedures which utilize high volume fluid flow rates.

As shown in FIG. 7, the distal end of the catheter assembly 10 includes a tip member 14 which may be partially formed by a stepped section 27 and a blunt end 29. The blood return lumen 26 extends longitudinally all the way through the body portion 12 and tip member 14 of the catheter assembly 10 so that it forms a distal opening 28 on the blunt end 29 of the tip member 14. The preferred cross-sectional shape of the lumen 26 is generally maintained as a D-shaped cross-sectional shape throughout the body portion 12 and the tip member 14 to open at the distal opening 28 although the cross-sectional shape of the lumen 26 may be transitioned to a circular cross-section in the tip member 14 or other shape as desired. The cross-sectional diameter of the distal opening 28 is preferably maximized so that the blood return lumen 26 may not require a side opening therein. In order to provide longitudinal spacing between the distal openings of the two lumens 24 and 26, the blood intake lumen 24 is terminated at side opening 30 in the stepped section 27 of the sidewall of the catheter.

At the proximal end portion of the body portion 12 of the catheter 10, the two D-shaped lumens 24 and 26 are connected to the hub member 16 which is described in more detail herein. The hub member 16 generally consists of a tubular member 32 which is adapted to surround a portion of the lumens of the catheter at the intersection of the body portion 12 of the catheter assembly 10 and the extension members 18 and 20. A pair of connectors 37 and 38 interconnect the proximal end of the body portion 12 with the distal end of the extension members 18 and 20 to provide continuous flow communication through the hub member 16. In the present embodiment, the connectors 37 and 38; the proximal end of the body portion 12; the distal end of the extension members 18 and 20 are then glued or otherwise bonded together and surrounded by the tubular member 32.

A pair of preferably resilient loop shaped members 34 and 36 extend from the sides of the tubular member 32. In the embodiment shown in FIGS. 7–10, the loop members 34 and 36 are preferably integral with and attached to the tubular member 32 to form enlarged openings between the loop members 34 and 36, respectively and the tubular body 32 to provide enlarged securement areas 40 on each side of the tubular body 32. As shown, the securement areas 40 of the present embodiment are preferably generally U-shaped and have an area which is significantly greater than the cross-sectional area of the loop shaped members 34 and 36. The enlarged securement areas 40 of the present invention provide one of the fundamental differences between the present invention and the prior art hub members or suture wings shown in FIGS. 1–6. In the preferred form of the present embodiment, the area of the securement area is preferably more than twice the cross-sectional area of the loop members 34 and 36 and more preferably nearly three, and most preferably, four times the cross-sectional area of the loop members 34 and 36. Additionally, the respective comparisons may also be preferably directed to average cross-sectional diameter of the loop members 34 and 36 such that the cross-sectional diameter of the loop members 34 and 36 may be varied if desired.

Figure 9:
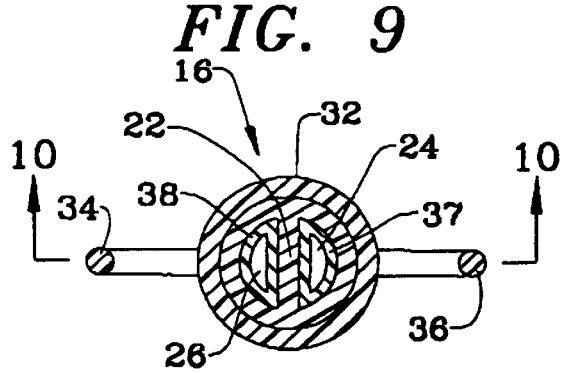
FIG. 9 is a cross-sectional view of the catheter hub member embodiment shown in FIG. 7 taken generally along lines 9—9 of FIG. 8.
Figure 10:
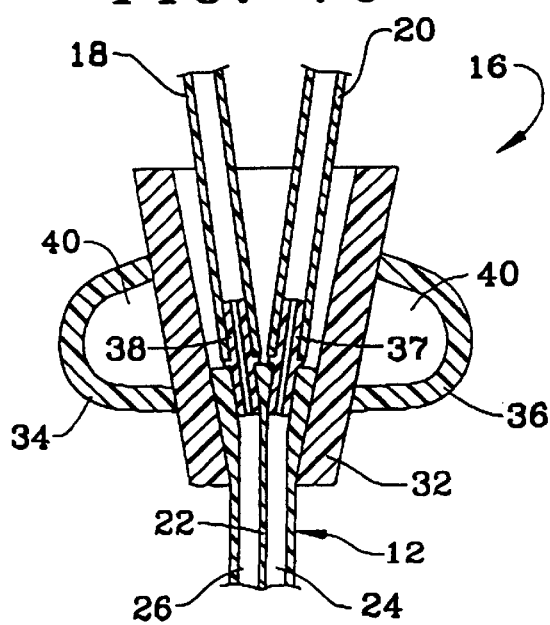
FIG. 10 is a longitudinal cross-sectional view of the catheter hub member embodiment shown in FIG. 7 taken generally along lines 10—10 of FIG. 9.

Additionally, each of the loop members 34 and 36 preferably extend laterally from the tubular member 32 a distance which is approximately equal to the outer diameter of the tubular member 32 to minimize the likelihood that the tubular member 32 or the body portion of the catheter assembly 10 will be nicked or damaged during insertion, use or removal. For example, in one embodiment of the present invention, the cross sectional diameter of the loop members 34 and 36 are about one-half of the diameter of the securement area 40 while the external diameter of the tubular member 32 is approximately equal to the diameter of the securement area 40. As shown in FIG. 9, the loop members 34 and 36 are preferably formed as solid members to increase the rigidity thereof. Alternately, it is anticipated that the loop members 34 and 36 may be formed as hollow members to increase the flexibility thereof. Additionally, the loop members 34 and 36 may alternately have cross sectional shapes other than the circular shapes shown generally in FIGS. 8 and 11 without adversely affecting the function thereof.

The extension members 18 and 20 are connected to conventional tubes leading to a dialysis unit(not shown), and include a pair of clamp members 42 and 44 for controlling the flow of fluids through the blood intake and return lumens 24 and 26. The extension members 18 and 20 are preferably soft and flexible so that they may be manipulated as needed and also easily closed by the pressure of the clamps 42 and 44. As shown in FIG. 7, the preferred form of the extension members 18 and 20 is generally straight although a precurved or bent configuration may be used to facilitate the positioning of the extension members 18 and 20 flat against the body of the patient when the catheter assembly 10 is inserted therein. A pair of luer connectors 43 and 45 are inserted onto the proximal end of the extension members 18 and 20 to serve as a means for coupling the proximal ends of the extension members 18 and 20 to a plurality of flexible tubes (not shown) which lead to the extracorporeal or hemodialysis treatment unit.

As shown in FIGS. 11–14, a modified hub member 50 in accordance with the present invention may also be used on single or multiple lumen catheters; including a double lumen catheter assembly 52 of the type shown and described herein. As with the embodiment described above and shown in FIGS. 7–10, the hub member 50 of the present embodiment is adapted for use on nearly any catheter although it is preferably used on longer term catheters such as hemodialysis or apheresis catheters. Like numbers have been added to like members which are more fully described above. In this embodiment, the catheter assembly 52 includes a septum 54 of nearly any shape which separates first and second lumens, 56 and 58, respectively. In this embodiment, the cross-sectional shape of the body portion 12 of the catheter assembly 52 is preferably oval. Additionally, the cross-sectional shape of the lumens 56 and 58 are preferably circular.

Figure 11:
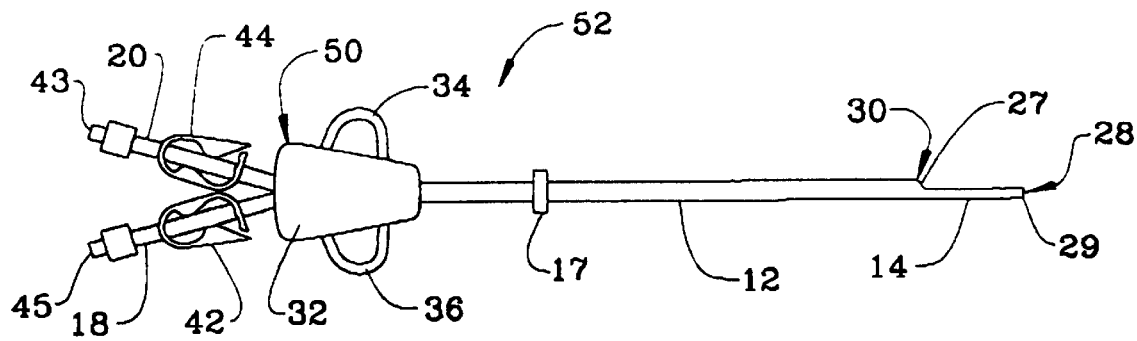
FIG. 11 is an elevated side view of an alternate embodiment of the catheter and hub member of the present invention thereon.
Figure 12:
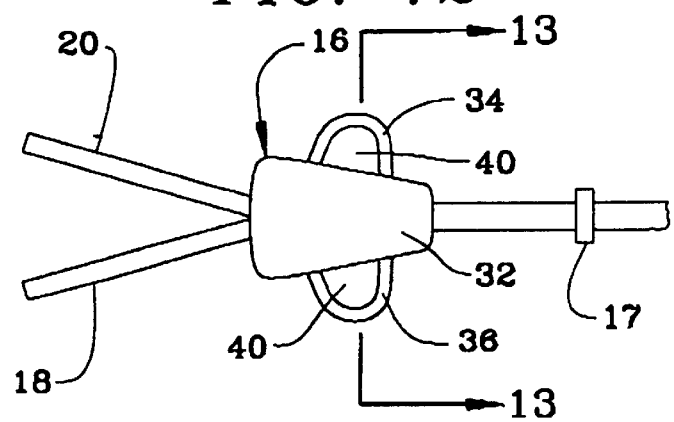
FIG. 12 is an enlarged side view of the catheter of the embodiment shown in FIG. 11 showing an alternate embodiment of the catheter hub member of the present invention.

The catheter assembly 52 of this embodiment generally includes an elongate body portion 12 having a tip member 14 on the distal end thereof and a Y-shaped connector or hub member 16 on the proximal end thereof. As shown in FIG. 11, the catheter assembly 52 of the present embodiment also preferably includes cuff member 17 on the body portion 12 and is particularly useful for long term use; i.e., implantation in excess of thirty days. As shown in FIG. 11, the proximal end of the hub member 16 includes extension members 18 and 20 thereon.

As shown in FIG. 11, the distal end of the catheter assembly 52 includes a tip member 14 which may be partially formed by a stepped section 27 and a blunt end 29. The second lumen 58 extends longitudinally all the way through the body portion 12 and tip member 14 of the catheter assembly 10 so that it forms a distal opening 28 on the blunt end 29 of the tip member 14. The preferred cross-sectional shape of the second lumen 58 is generally maintained as a round cross-sectional shape throughout the body portion 12 and the tip member 14 to open at the distal opening 28. The cross-sectional diameter of the distal opening 28 is preferably maximized so that the second lumen 58 may not require a side opening therein. In order to provide longitudinal spacing between the distal openings of the two lumens 56 and 58, the first lumen 56 is terminated at side opening 30 in the stepped section 27 of the sidewall of the catheter.

At the proximal end portion of the body portion 12 of the catheter assembly 52, the two round lumens 56 and 58 are connected to the hub member 50 which is described in more detail herein. The hub member 50 generally consists of a tubular member 32 which is adapted to surround a portion of the lumens of the catheter at the intersection of the body portion 12 of the catheter assembly 52 and the extension members 18 and 20. A pair of connectors 37 and 38 interconnect the proximal end of the body portion 12 with the distal end of the extension members 18 and 20 to provide continuous flow communication through the hub member 50. In the present embodiment, the connectors 37 and 38; the proximal end of the body portion 12; the distal end of the extension members 18 and 20 are then glued or otherwise bonded together and surrounded by the tubular member 32.

As with the prior embodiment, a pair of preferably resilient loop shaped members 34 and 36 extend from the sides of the tubular member 32. In the embodiment shown in FIGS. 11–14, the loop members 34 and 36 are preferably integral with and attached to the tubular member 32 to form enlarged openings between the loop members 34 and 36, respectively and the tubular body 32 to provide enlarged securement areas 40 on each side of the hub member 50. As shown, the securement areas 40 of the present embodiment are preferably generally U-shaped and have an area which is significantly greater than the cross-sectional area of the loop shaped members 34 and 36. The enlarged securement areas 40 of the present embodiment provide one of the fundamental differences between the present invention and the prior art hub members or suture wings shown in FIGS. 1–6. In the preferred form of the present embodiment, the area of the securement area is preferably more than twice the cross-sectional area of the loop members 34 and 36 and more preferably nearly three, and most preferably, four times the cross-sectional area of the loop members 34 and 36.

Additionally, each of the loop members 34 and 36 preferably extend laterally from the tubular member 32 a distance which is greater thawing the outer lateral diameter of the tubular member 32 to minimize the likelihood that the tubular member 32 or the body portion of the catheter assembly 52 will be nicked or damaged during insertion, use or removal. For example, in one embodiment of the present invention, the cross sectional diameter of the loop members 34 and 36 are about one-half of the diameter of the securement area 40 while the external diameter of the tubular member 32 is approximately equal to or slightly greater than the diameter of the securement area 40. As shown in FIG. 13, the loop members 34 and 36 are preferably formed as solid members to increase the rigidity thereof.

As with the prior embodiment, the extension members 18 and 20 are connected to conventional tubes leading to a dialysis unit (not shown), and include a pair of clamp members 42 and 44 for controlling the flow of fluids through the blood intake and return lumens 24 and 26. The extension members 18 and 20 are preferably soft and flexible so that they may be manipulated as needed and also easily closed by the pressure of the clamps 42 and 44. As shown in FIG. 11, the preferred form of the extension members 18 and 20 is generally straight although a pre-curved or bent configuration may be used to facilitate the positioning of the extension members 18 and 20 flat against the body of the patient when the catheter assembly 10 is inserted therein. A pair of luer connectors 43 and 45 are inserted onto the proximal end of the extension members 18 and 20 to serve as a means for coupling the proximal ends of the extension members 18 and 20 to a plurality of flexible tubes (not shown) which lead to the extracorporeal or hemodialysis treatment unit.

Figure 15:
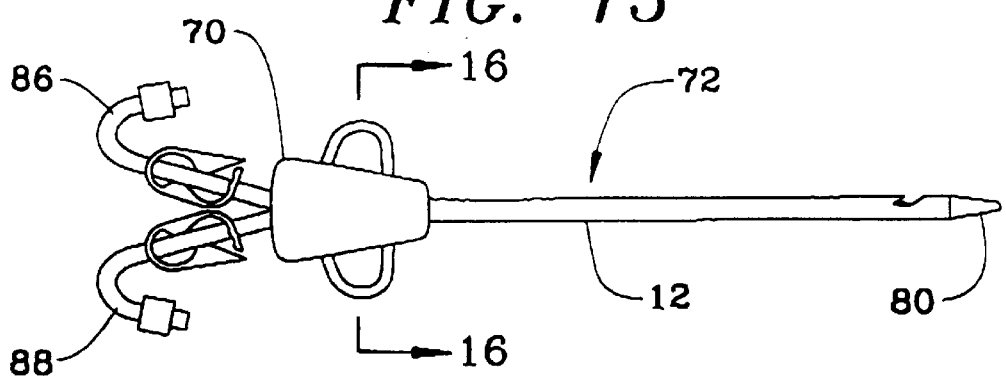
FIG. 15 is an elevated side view of an alternate embodiment of the catheter and hub member of the present invention.
Figure 16:
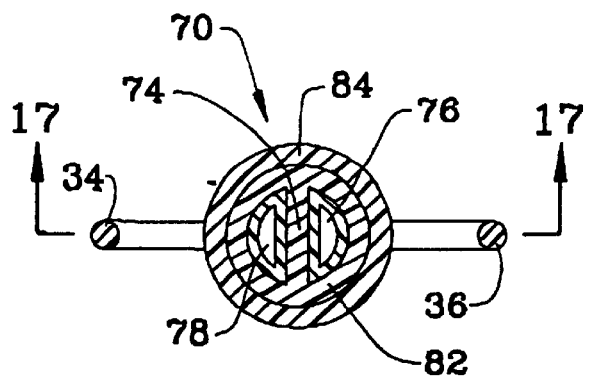
FIG. 16 is an enlarged side view of the catheter hub member of FIG. 15.
Figure 17:
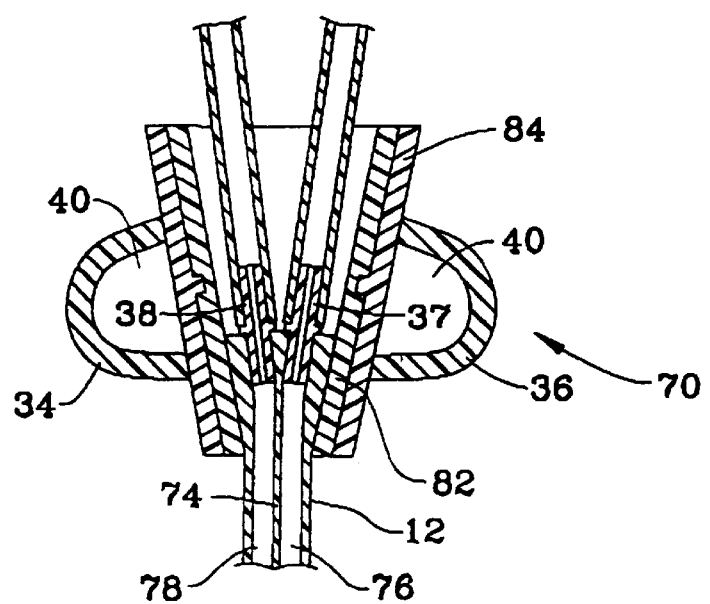
FIG. 17 is an enlarged cross sectional view of the catheter hub member shown in FIG. 15 taken generally along lines 17—17 of FIG. 16.

As shown in FIGS. 15–17, a modified hub member 70 in accordance with the present invention may also be used on single or multiple lumen catheters; including a double lumen catheter assembly 72 of the type shown and described herein. The hub member 70 of the present embodiment is adapted for use on nearly any catheter although it is preferably used on shorter term catheters such as infusion or central venous access catheters. Like numbers have been added to like members which are more fully described above. In this embodiment, the catheter assembly 72 includes a septum 74 which separates first and second lumens, 76 and 78, respectively. In this embodiment, the cross-sectional shape of the body portion 12 of the catheter assembly 72 is preferably round and the cross-sectional shape of the lumens 76 and 78 are preferably generally D-shaped.

At the distal end of the catheter assembly 10, the exterior surface of the body portion 12 merges into a tip member 80 which may be a smoothly tapered conical member. On the inside of the body portion 12, the second lumen 78 extends longitudinally all the way through the tip member 80, bending slightly as it passes through the tip member 80 so that it opens at distal opening 28 near the center of the distal end of the tip member 80. Within the tip member 80 the preferred cross-sectional shape of the lumen 78 gradually changes from D-shaped at the proximal end of the tip member 80 to circular cross-sectional shape at the distal end of the tip member 80 at the distal opening 28. The cross-sectional diameter of the distal opening 28 is preferably maximized so that a side opening is preferably not required. In order to provide longitudinal spacing between the distal openings of the two lumens 76 and 78, the first lumen 76 is terminated at a side opening 30 in the sidewall of the body portion 12 of the catheter assembly 72.

At the proximal end portion of the body portion 12 of the catheter assembly 72, the two D-shaped lumens 76 and 78 connect to the hub member 70 of the present embodiment which is described in more detail herein. The hub member 70 generally consists of a sleeve member 82 which is surrounded by the tubular member 84. The sleeve member 82 is adapted to enclose the lumens of the catheter at the intersection of the catheter body and the extension members with the hub member 70. The tubular member 84 preferably surrounds the sleeve member 82 and is rotatable with respect thereto. A pair of preferably resilient loop shaped members 34 and 36 extend from the sides of the tubular member 84. The loop members 34 and 36 of the present embodiment are preferably integral with and attached to the tubular member 84 to form enlarged openings between the loop members 34 and 36, respectively and the tubular member 84 to provide a enlarged securement areas 40 therebetween. As with the prior embodiments and as shown best in FIGS. 15 and 16, the openings of the securement area 40 are preferably at least twice as large as the average cross-sectional diameter of the loop members 34 or 36, and, in any event are significantly larger than the currently available hub members or suture wings as shown in FIGS. 1–6. The loop members 34 and 36 are relatively soft and flexible and are spaced apart a significant distance from the tubular member 84 or main portion of the hub member 70 in addition to being rotatable with respect to the body portion of the catheter.

At the proximal end portion of the body portion 12 of the catheter assembly 72, the two lumens 76 and 78 are connected to the hub member 70 which is described in more detail herein. The hub member 70 generally consists of the tubular member 84 which is adapted to rotatably surround the sleeve member 82. The sleeve member 82 surrounds a portion of the lumens of the catheter assembly 72 at the intersection of the body portion 12 of the catheter assembly 82 and the extension members 18 and 20. A pair of connectors 37 and 38 interconnect the proximal end of the body portion 12 with the distal end of the extension members 18 and 20 to provide continuous flow communication through the hub member 70. In the present embodiment, the connectors 37 and 38; the proximal end of the body portion 12; the distal end of the extension members 18 and 20 are then glued or otherwise bonded together and surrounded by the sleeve member 82.

As with the prior embodiments, a pair of preferably resilient loop shaped members 34 and 36 extend from the sides of the tubular member 84. In the embodiment shown in FIGS. 15–17, the loop members 34 and 36 are preferably integral with and attached to the tubular member 84 to form enlarged openings between the loop members 34 and 36, respectively and the tubular body 84 to provide enlarged securement areas 40 on each side of the hub member 70. As shown, the securement areas 40 of the present embodiment are preferably generally U-shaped and have an area which is significantly greater than the cross-sectional area of the loop shaped members 34 and 36. The enlarged securement areas 40 of the present embodiment provide one of the fundamental differences between the present invention and the prior art hub members or suture wings shown in FIGS. 1–6. In the preferred form of the present embodiment, the area of the securement area 40 is preferably more than twice the cross-sectional area of the loop members 34 and 36 and more preferably nearly three, and most preferably, four times the cross-sectional area of the loop members 34 and 36.

Additionally, each of the loop members 34 and 36 preferably extend laterally from the tubular member 84 a distance which is greater than the outer lateral diameter of the tubular member 84 to minimize the likelihood that the tubular member 84 or the body portion of the catheter assembly 72 will be nicked or damaged during insertion, use or removal.

To facilitate connection of the hub member 70 to the conventional tubes leading to a dialysis unit, the hub member 70 of the presently embodiment is preferably attached to the generally pre-curved or bent pair of tubular extension members 86 and 88 as shown generally in FIG. 15. These extension members 86 and 88 are relatively soft and flexible so that they may be manipulated as needed and also easily closed by the pressure of the clamps 42 and 44. As shown in FIG. 15, the preferred form of the extension members of this embodiment facilitate the positioning of the extension members 86 and 88 flat against the body of the patient. The clamps 42 and 44 serve as on-off valves for controlling the flow of blood between the catheter assembly 72 and the dialysis unit. A pair of luer connectors are inserted on the proximal end of the extension members 86 and 88. The luer connectors serve as a means for coupling the proximal ends of the extension members 86 and 88 to a plurality of flexible tubes (not shown) which lead to the extracorporeal or hemodialysis treatment unit.

Figure 18:
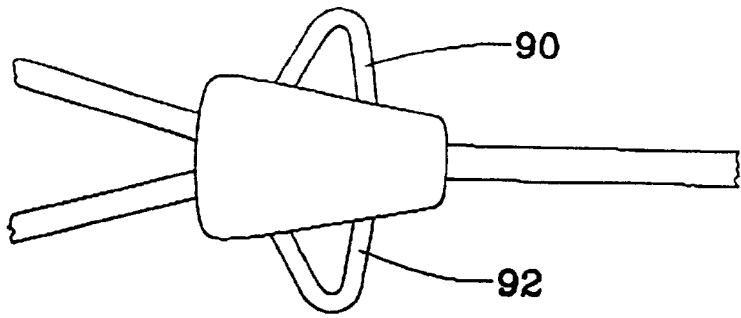
FIG. 18 is an elevated side view of an alternate embodiment of the catheter and hub member of the present invention.

FIG. 18 is illustrative of an alternate embodiment of the present invention wherein like numbers have been added to like members which are described above. As shown in FIG. 18, the loop members 90 and 92 have a generally triangular shape as shown in the elevated view.

Figure 19:
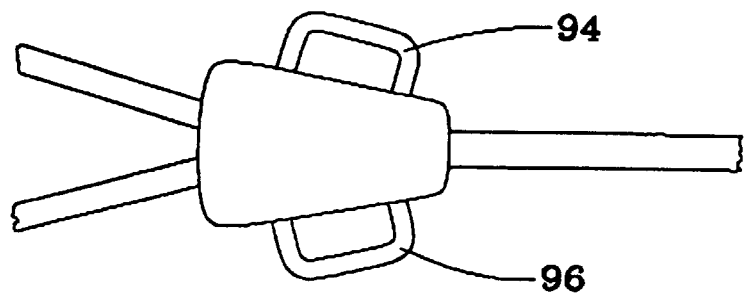
FIG. 19 is an elevated side view of an alternate embodiment of the catheter and hub member of the present invention.

FIG. 19 is illustrative of an alternate embodiment of the present invention wherein like numbers have been added to like members which are described above. As shown in FIG. 19, the loop members 94 and 96 have a generally square or rectangular shape as shown the in elevated view.

Figure 20:
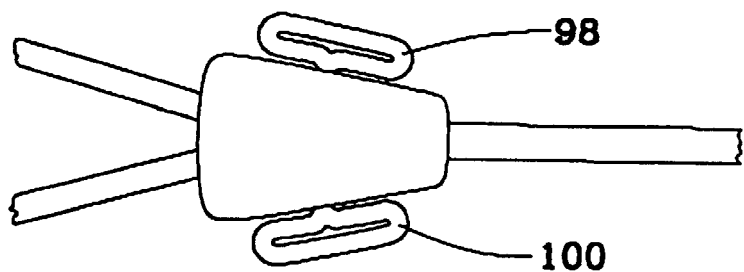
FIG. 20 is an elevated side view of an alternate embodiment of the catheter and hub member of the present invention wherein the loop members are shown in a relaxed, non-extended position.
Figure 21:
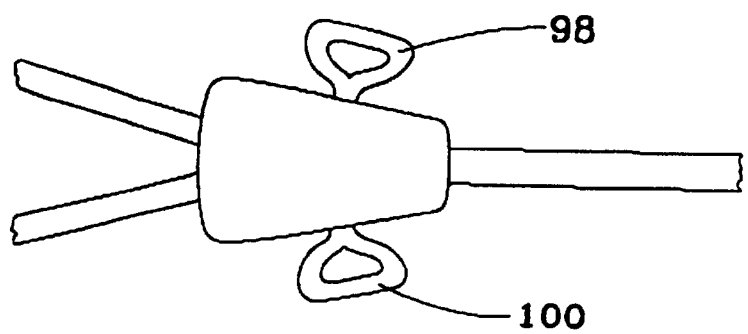
FIG. 21 is an elevated side view of the alternate embodiment of the catheter and hub member shown in FIG. 20 wherein the loop members are shown in a stretched and extended position.

FIGS. 20–21 are illustrative of an alternate embodiment of the present invention wherein like numbers have been added to like members which are described above. As shown in FIG. 20, the loop members 98 and 100 have a generally collapsed oblong shape as shown in the elevated view. In this embodiment, the loop members 98 and 100 provide increased flexibility and lateral extension to accommodate patient movement while providing the benefits and advantages described above for the various embodiments of the present invention.

While the foregoing description has been drawn to the presently preferred embodiments of the present invention, it should be understood by those skilled in the art of the present subject matter that various modifications may be made to the present invention without departing from the scope and spirit of the invention which is defined by the following claims.

What is claimed is:

1. An elongate catheter for use in the treatment of a patient, said catheter comprising:
   an elongate and tubular catheter body portion formed by a circumferential sidewall and having a longitudinal axis and distal and proximal end portions thereon;
   a hub member attached to said body portion at said proximal end portion thereof;
   said hub member including a generally tubular body portion thereof;
   at least one loop member having a cross sectional dimension and first and second end portions integral with said tubular body portion of said hub member to form an enclosed opening between said tubular body portion of said hub member and said at least one loop member such that said opening defines an area which is greater than said cross sectional dimension of said at least one loop member to form an enlarged securement area therebetween.

2. The elongate catheter of claim 1 wherein said tubular body portion is a generally elongate and cylindrical member and said at least one loop member extends laterally therefrom.

3. The elongate catheter of claim 2 wherein said tubular body portion includes an outer diameter and said at least one loop member extends laterally from said tubular body portion a distance which is greater than said diameter of said tubular body portion.

4. The elongate catheter of claim 1 wherein said at least one loop member is generally U-shaped.

5. The elongate catheter of claim 1 wherein said area of said opening is approximately twice the cross-sectional dimension of said at least one loop member.

6. The elongate catheter of claim 1 wherein said at least one loop member includes at least a portion thereof which extends laterally from said tubular body portion and said area of said opening is approximately twice the cross-sectional dimension of at least said laterally extending portion of said at least one loop member.

7. The elongate catheter of claim 1 wherein said tubular body portion has a cross-sectional area which is greater than said cross-sectional dimension of said at least one loop member.

8. An elongate catheter for use in the treatment of a patient, said catheter comprising:
   an elongate and tubular catheter body portion formed by a circumferential sidewall and having a longitudinal axis and distal and proximal end portions thereon;
   a hub member having a tubular portion and an outer diameter and said tubular portion of said hub member is attached to said body portion at said proximal end portion thereof;
   at least one loop member integral with said tubular portion of said hub member and having a cross sectional area and extending laterally from said tubular portion of said hub member to form an enclosed opening between said tubular portion of said hub member and said at least one loop member having an area therebetween such that said at least one loop member extends laterally from said tubular portion of said hub member a greater distance than the outer diameter of said tubular portion of said hub member to form an enlarged securement area therebetween and the area of said opening is greater than said cross sectional area of said at least one loop member.

9. The elongate catheter of claim 8 wherein said at least one loop member consists of a pair of loop members extending laterally from said tubular portion.

10. The elongate catheter of claim 8 wherein said at least one loop member is generally U-shaped.

11. The elongate catheter of claim 8 wherein the area of said opening is greater than twice said cross sectional area of said at least one loop member.

12. The elongate catheter of claim 8 wherein said area of said opening is greater than four times said cross sectional area of said at least one loop member.

13. The elongate catheter of claim 8 wherein said tubular portion has a cross sectional area which is greater than said cross sectional area of said at least one loop member.

14. An elongate catheter for use in the treatment of a patient, said catheter comprising:
   an elongate and tubular catheter body portion formed by a circumferential sidewall and having a longitudinal axis and distal and proximal end portions thereon;
   a hub member including a generally tubular portion and wherein said hub member is attached to said body portion at said proximal end portion thereof; and
   at least one generally U-shaped loop member integral with said tubular portion of said hub member and having distal and proximal end portions connected to said hub member and a cross sectional area and wherein said at least one generally U-shaped member extends laterally from said tubular portion of said hub member to form a generally U-shaped and enclosed securement area between said tubular portion of said hub member and said at least one U-shaped loop member.

15. The elongate catheter of claim 14 wherein said securement area forms an opening having an area which is greater than said cross sectional area of said at least one U-shaped loop member to form said enlarged securement area therebetween.

16. The elongate catheter of claim 14 wherein said at least one U-shaped loop member consists of a pair of generally U-shaped loop members which each extend laterally from said tubular portion and said pair of generally U-shared loop members include a generally circular cross section.

17. The elongate catheter of claim 14 wherein the area of said securement area is greater than twice said cross sectional area of said at least one loop member.

18. An elongate catheter for use in the treatment of a patient, said catheter comprising:

an elongate and tubular catheter body portion formed by a circumferential sidewall and having a longitudinal axis and distal and proximal end portions thereon;

a hub member including a generally tubular portion and wherein said hub member is attached to said body portion at said proximal end portion thereof;

at least one generally U-shaped loop member having distal and proximal end portions integral with said tubular portion of said hub member and a cross sectional area and wherein said at least one generally U-shaped member extends laterally from said tubular portion of said hub member to form a generally U-shaped and enclosed securement area between said tubular portion of said hub member and said at least one U-shaped loop member; and wherein said tubular portion is a generally elongate and cylindrical member and said at least one U-shaped loop member includes a pair of U-shaped loop members which each extend laterally from said hub member.

19. The elongate catheter of claim 18 wherein said tubular portion includes an outer diameter and said pair of U-shaped loop members extend laterally from said tubular portion a distance which is greater than said outer diameter of said tubular portion.

20. An elongate catheter for use in the treatment of a patient, said catheter comprising:

an elongate and tubular catheter body portion formed by a circumferential sidewall and having a longitudinal axis and distal and proximal end portions thereon;

a hub member attached to said body portion at said proximal end portion thereof and said hub member including a generally elongate and cylindrical tubular portion thereon and said tubular portion having an outer diameter; and a pair of generally U-shaped loop members having a cross sectional dimension and being integral with and extending laterally from said tubular portion of said hub member to form a plurality of enclosed openings between said tubular portion of said hub member and said loop members such that of each of said openings defines an area which is greater than said cross sectional dimension of said loop members and said loop members extend laterally from said tubular portion of said hub member a greater distance than said outer diameter of said tubular portion to form an enlarged securement area therebetween.

* * * * *